United States Patent
Pittaro et al.

(10) Patent No.: US 6,640,197 B2
(45) Date of Patent: Oct. 28, 2003

(54) SELF ALIGNING SENSOR ARRAY SYSTEM

(75) Inventors: Richard J. Pittaro, San Carlos, CA (US); David Andrew King, Menlo Park, CA (US); Richard D. Pering, Mountain View, CA (US); Shahida Rana, Fremont, CA (US); Frederick A. Stawitcke, Sunnyvale, CA (US); Edward Verdonk, San Jose, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 10/072,240

(22) Filed: Feb. 8, 2002

(65) Prior Publication Data

US 2003/0154046 A1 Aug. 14, 2003

(51) Int. Cl.$^7$ .................. G01C 25/00; G01N 21/75
(52) U.S. Cl. .............. 702/116; 356/128; 356/445; 359/622; 385/88; 385/89; 436/518; 250/458.1
(58) Field of Search ................. 702/20, 31, 116; 250/458.1, 491.1; 385/88, 89; 356/128, 445; 349/95; 359/622; 436/518

(56) References Cited

U.S. PATENT DOCUMENTS

| | | | | |
|---|---|---|---|---|
| 4,997,278 A | * | 3/1991 | Finlan et al. | 356/128 |
| 5,255,075 A | * | 10/1993 | Cush | 356/445 |
| 6,251,688 B1 | * | 6/2001 | Erb et al. | 436/518 |
| 6,473,238 B1 | * | 10/2002 | Daniell | 359/622 |

OTHER PUBLICATIONS

Anderson et al., "Optical transmitter, receiver" Pub. No: US 2002/0122637 A1, Filed Date: Dec. 26, 2000.*

Wichman et al., "Method to align optical components to a substrate" Pub. No.: US 2002/0034363 A1, Field Date: Aug. 2, 2001.*

* cited by examiner

Primary Examiner—John Barlow
Assistant Examiner—John Le

(57) ABSTRACT

A sensor array is bonded to or molded together with a micro-lens array to form a sensor cartridge. The micro-lenses of the micro-lens array are configured to focus light incident on the sensors, into the sensors. An alignment structure has a mating profile that receives and engages one or more micro-lenses from the micro-lens array to laterally align the cartridge to enable repeatable precise positioning of the cartridge.

18 Claims, 2 Drawing Sheets

SELF ALIGNING SENSOR ARRAY SYSTEM

BACKGROUND OF THE INVENTION

1. Technical Field of the Invention

The present invention relates in general to biochemical test equipment, and more particularly to alignment of sensor arrays in a biochemical testing device.

2. Description of Related Art

In a biochemical testing device for detecting and measuring luminescence, fluorescence, scattering, or absorption of analytes, one or more sensors in a sensor array is scanned to collect data from a sample. The sensors are biological or chemical substances deposited onto a substrate to form a sensor array. The biological or chemical substances can be chosen to bond with particular analytes or to react with particular analytes and change the sensor's optical properties after such reaction. The analytes usually include proteins, peptides, or DNA. For example, a biochemical fluorescence sensor has a biological binder used capture a particular analyte and enable detection and measurement of its fluorescence characteristics. Light of a pre-determined wavelength is directed onto the sensor to excite the captured analyte. The light causes the analyte to fluoresce, and the analyte's fluorescence is then detected and measured by a photo detector array, such as a CCD (charge coupled device) or a CMOS (complementary metal oxide semiconductor) array.

A moderately sized sensor array, for example 10 by 10, can contain 100 sensors. With so many sensors, it is difficult to direct concentrated light to each of the sensors to excite their respective analytes. The most simple way to provide light to the sensors is to flood illuminate the sensor array. However, when flood illuminating the array, much of the light is not directed at the sensors and is wasted.

Another way to provide light to the sensors is to direct a focused beam to each sensor. The light can be directed to each sensor by actively aiming the focused beam. For example, the light can be directed from a reflector system or from a diffraction grating having a diffraction pattern that matches the sensor locations. Either method, however, requires that the sensor array be precisely placed in relation to the device directing the focused light beam, or that the device directing the focused light beam have an active ability to correct for misalignment of the sensor array. Also, the specific position of each sensor must be known to correlate light emitted from a sensor with the light detected at the detector array.

In one prior art device, precision pins are registered into the sensor array. These pins are received in a structure that houses the light source and photo detector array to ensure precise placement of the sensor array relative to the light source and photo detector array. While such an alignment system is operable, it has several limitations. For example, when positioning the sensor array, care must be taken to ensure that the pins are fully received in the structure that houses the light source and photo detector array. If the pins are not fully received in the structure, the sensor array may be misaligned. Further, such pins must be precisely constructed and precisely placed with respect to the sensor array. Fabricating and placing the pins is an additional component and an additional step in manufacturing which increases the cost of constructing the sensor array.

There is a need for an improved mounting arrangement for aligning a sensor array in relation to the photo detector array or light source. Further, there is a need for a system to make precise alignment of the sensor array with the incident light less critical, thus compensating for slight misalignments.

SUMMARY OF THE INVENTION

The exemplary embodiments of the present invention encompass a sensor alignment system and a biochemical testing device having an improved mounting arrangement to align the sensor array in relation to a photo detector array and light source.

The biochemical testing device has a sensor cartridge with at least one sensor. At least one micro-lens is coupled to the sensor such that the micro-lens focuses light into the sensor. The micro-lens has an outer surface. The testing device has an alignment structure with a mating profile adapted to receive the outer surface of the micro-lens to position the sensor cartridge laterally. A light source illuminates the at least one micro-lens. At least one optical detector is positioned to detect light emitted from the at least one micro-lens.

The invention encompasses a sensor alignment system for aligning a sensor array in a biochemical testing device. The Sensor array has one or more micro lenses. The sensor alignment system has an alignment structure positioned in relation to the biochemical testing device and adapted to receive the one or more micro-lenses of the micro-lens array to align the biochemical testing device with the sensor array.

The invention also encompasses a biochemical testing device for receiving a sensor cartridge. The sensor cartridge having at least one sensor and at least one micro-lens coupled to the sensor. The testing device has an alignment structure having a mating profile adapted to receive the outer surface of the micro-lens to position the sensor cartridge laterally. A light source is positioned in relation to the alignment structure for illuminating the at least one micro-lens. The testing device also has at least one photo-detector positioned in relation to the alignment structure to detect light emitted from the at least one micro-lens.

Features and advantages of the invention will be come apparent to one skilled in the art upon examination of the following detailed description, when read in conjunction with the accompanying drawings.

BRIEF DESCRIPTION OF THE DRAWINGS

Various objects and advantages of the invention will become apparent and more readily appreciated from the following description of the presently preferred exemplary embodiments, taken in conjunction with the accompanying drawings of which.

DETAILED DESCRIPTION OF EXEMPLARY EMBODIMENTS OF THE INVENTION

Exemplary embodiments of the invention will now be described more fully with reference to the accompanying drawings. This invention may, however, be embodied in many different forms, and should not be construed as limited to the embodiments and preferred methods set forth herein.

Figure 1:
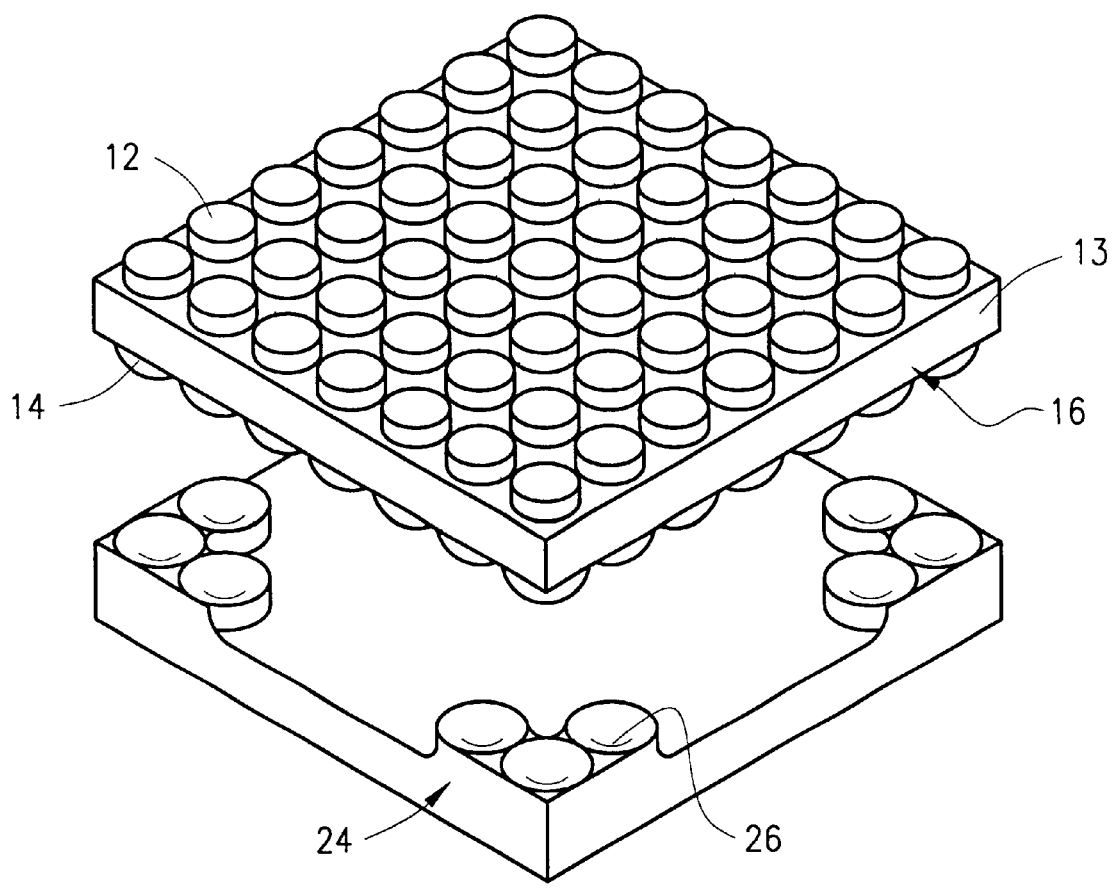
FIG. 1 is a perspective view of a sensor cartridge and an alignment structure constructed in accordance with the invention.

Referring first to FIG. 1, a sensor array 12 has at least one biochemical sensor or, more preferably, multiple biochemical sensors deposited onto a substrate 13. Sensors 12 can be, for example, biochemical sensors for measuring or detecting luminescence, fluorescence, scattering, absorption or other characteristics of biological or chemical samples. Each biochemical sensor in the array 12 comprises a biological or chemical substance that is adapted to selectively bind to or react with a pre-selected analyte for evaluation. The binder can be for example a protein or peptide. If the sensor 12 reacts with the analyte, the optical properties of the biological or chemical substance can change after the reaction.

The sensor array 12 is molded together with or bonded to one or more micro-lenses 14 to form a sensor cartridge 16. The micro-lenses 14 are preferably constructed from an optical quality glass or polymer, as is the substrate 13. The term micro-lens is used herein to indicate that the lenses correspond in number and position to sensors in the array 12. Thus, for every sensor contained in an array 12, there is preferably a micro-lens 14 aligned to focus light into the sensor. As such, a micro-lens is usually smaller (i.e. micro) than a lens that would be used in focusing light to the entire sensory array 12. While the concepts described herein are disclosed with respect to a sensor array 12 having micro-lenses 14, they are equally applicable to and the invention is intended to encompass other lens configurations.

The alignment of the micro-lenses 14 and their respective sensor 12 can be controlled very precisely when the micro lenses 14 are molded into the structure of the substrate 13, using precision molding techniques known in the art. In an embodiment where the micro-lenses 14 are bonded into the substrate 13, pre-fabricated micro-lenses 14 can be used. The precision placement of the micro-lenses 14 with respect to the sensors 12 can also be very closely controlled by precisely positioning the micro-lenses 14 with respect to the sensors 12 when bonding them into the substrate 13.

Each micro lens 14 is configured to focus light into its respective sensor 12. This provides increased illumination of the sensor 12, as compared to a sensor without a micro-lens, because light directed at the sensor 12 is focused directly into the sensor 12. Further, light emitted from the analyte or sensor 12 is projected into a predictable pattern by the micro-lens 14. Such patterning aids in detection and measurement of the emitted light, because it facilitates correlating the emitted light with a particular sensor 12. Also, because the micro-lenses 14 are close to their respective sensors 12, they are able to gather more of the light emitted from the analyte and transmit a more intense light for detection and measurement.

Figure 2A:
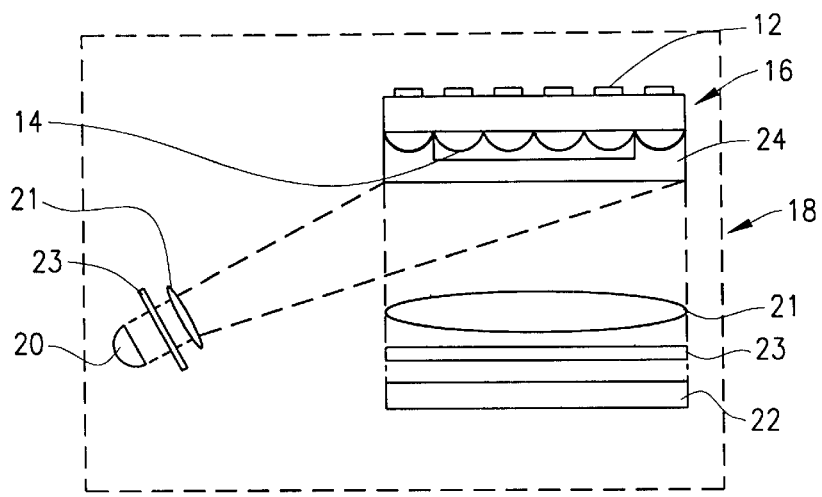
FIGS. 2A–C are exemplary schematics of scanner devices utilizing flood and focused beam illumination of their respective sensor cartridges in accordance with the invention.
Figure 2B:
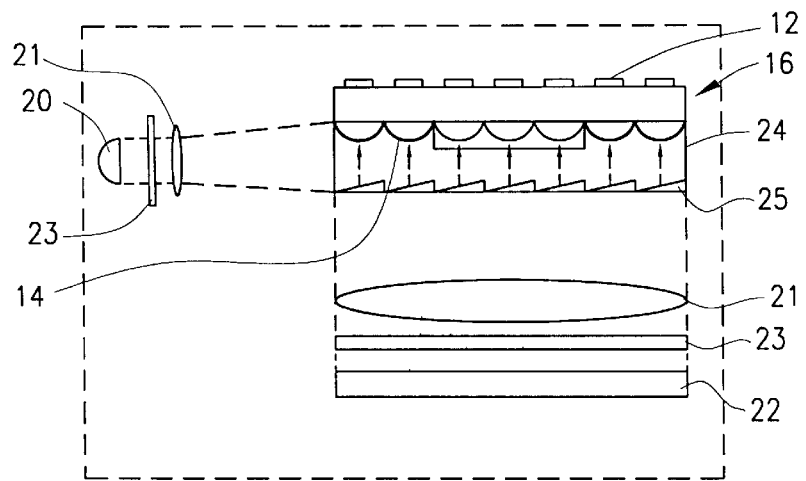
Figure 2C:
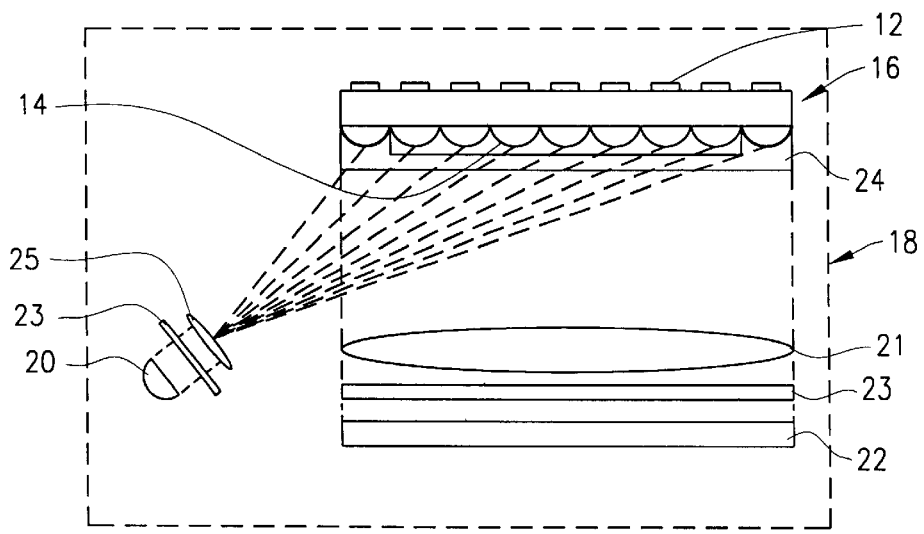

Referring to FIGS. 2A–C, the cartridge 16 is adapted to be received in a scanner device 18. The scanner device 18 is a test instrument that reads the data from the sensors 12 and processes the data into a user readable format or transmits the data to a device that can process the data into a user readable format. The scanner device 18 contains a light source 20 for illuminating the micro-lenses 14, and thus the sensors 12. A photo detector array 22, such as a CCD or CMOS array, is provided for detecting and measuring the light emitted from the micro-lenses 14. One or more lenses 21 can be provided between the cartridge 16 and the photo detector array 22 to further focus and guide light emitted from the micro-lenses 14 into the photo detector array 22. Also, one or more lenses 21 can be provided at the light source 20 to focus and guide its illumination. A filter 23 adapted to block particular wavelengths of light can be provided at the light source 20 to control the wavelength of the light that illuminates the sensors 12. A filter 23 can be provided at the photo detector array 22 to filter out unwanted wavelengths and ensure that only desired wavelengths are detected at the photo detector array 22. Finally, the scanner device 18 contains an alignment structure 24 that receives and precisely positions the cartridge 16.

Referring again to FIG. 1, the outer surface of each micro-lens 14 is preferably convex. The alignment structure 24 has a mating profile 26 that is preferably concave and shaped to closely receive the profile of one or more micro-lenses 14. It is also preferred that the micro-lenses 14 and the mating profile 26 are each substantially hemispherical to provide relatively deep, substantially symmetrical or semi-symmetrical profile that will promote alignment. It is not necessary for the purposes of this invention, however, that the micro-lenses 14 and the mating profile 26 be truly hemispheric or consist of a complete hemisphere. It is also possible that the outer surface of the micro-lenses 14 be concave. If the outer surface is concave, then the mating profile 26 is preferably convex.

In a cartridge 16 with many micro-lenses 14, it is preferable that the mating profile 26 not receive all of the micro-lenses 14, because it would difficult to accurately match the pattern of the mating profile 26 and micro-lenses 14. Further, aligning with more than a few micro-lenses 14 is redundant. Thus, the mating profile 26 is provided to receive preferably only a subset of the micro-lenses 14.

As the cartridge 16 is received into the alignment structure 24, the substantially hemispherical micro-lenses 14 center in the substantially hemispherical profile 26 and laterally align the cartridge 16 relative to the alignment structure 24. The position of alignment structure 24 can be fixed relative to the photo detector array 22 to enable correlation of light detected at the array 22 and sensors 12. If needed, the light source 20 can also be precisely positioned relative to the alignment structure 24. It is preferable, that the cartridge 16 be biased into the alignment structure 24 when in use, to ensure that the cartridge 16 remains aligned.

The alignment structure 24 can be transparent or translucent to allow light from the light source 20 to pass therethrough. Thus, the alignment structure 24 will transmit light to the micro-lenses 14, that will focus the light directly onto the sensors 12.

FIG. 2A depicts an exemplary flood illumination arrangement. In this configuration, the light source 20 is directed generally at the alignment structure 24. A lens 21 can be provided between the light source 20 and the alignment structure 24 to focus and guide the light from the light source 20 to the alignment structure 24. Also, a filter 23 can be provided between the light source 20 and alignment structure 24 to filter out unwanted wavelengths of light. The alignment structure 24 transmits light to the micro-lenses 14, and the micro-lenses 14 focus the light into each sensor 12. Light emitted from the sensors 12 is then directed out through micro-lenses 14 and alignment structure 24 onto the photo detector array 22. An additional lens 21 can be provided between the alignment structure 24 and the photo detector array 22 to focus and guide light onto the photo detector array 22. In this configuration, precision alignment of the light source 20 with the cartridge 16 is not critical. Also, because the light is focused into the sensors 12 by the micro-lenses 14, very little light is not focused or directed onto a sensor.

FIGS. 2B and C depict an exemplary scanner device 18 using directional beam illumination. The scanner device 18 of FIGS. 2B and C each have a diffraction grating 25 with a diffraction pattern matching the micro-lens 14 locations. Thus, light from the light source 20 is diffracted and projected through the alignment structure 24 and into the micro-lenses 14. The focus of the micro-lenses 14 will compensate for some amount of horizontal misalignment, because light which is not directed to the center of the sensor 12 will be focused toward the sensor's 12 center by the micro-lenses 14. However, precise placement of the cartridge 16 with respect to the diffraction grating 25 can be achieved by precisely positioning the alignment structure 24 in relation to the diffraction grating 25. Thus, when the cartridge 16 is received in the alignment structure 24, the alignment structure 24 will position the cartridge 16 laterally to ensure alignment of the diffraction grating 25 and sensors 12.

Embodiments of the invention have significant advantages. Integrating the micro-lenses and sensors into a single cartridge enables precise alignment of the micro-lenses and sensors whether bonded or molded into the cartridge. Utilizing micro-lenses with the sensors focuses diffuse light into the sensors and compensates for horizontal misalignment of light directed at the sensors. This eliminates the need for precise alignment of the sensor array with the light source. Alternately, it eliminates the need for a complex system that can actively compensate for misalignment of the sensor array. Finally, utilizing the micro-lenses for alignment reduces the number of components used in aligning the sensor array as the lenses perform the dual function of alignment and focusing the light into the sensors.

It is to be understood that while the invention has been described above in conjunction with preferred exemplary embodiments, the description and examples are intended to illustrate and not limit the scope of the invention. That which is described herein with respect to the exemplary embodiments can be applied to the construction of many different types of devices. Thus, the scope of the invention should only be limited by the following claims.

We claim:

1. A biochemical testing device comprising:
   a sensor cartridge having at least one sensor and at least one micro-lens physically coupled to the sensor such that the micro-lens focuses light into the sensor, the micro-lens having an outer surface,
   an alignment structure having a mating profile adapted to receive the outer surface of the micro-lens to position the sensor cartridge laterally;
   a light source for illuminating the at least one micro-lens; and
   at least one photo detector positioned to detect light emitted from the at least one micro-lens.

2. The device of claim 1 wherein the at least one micro-lens is molded together with the at least one sensor.

3. The device of claim 1 wherein the at least one micro-lens is bonded to the at least one sensor.

4. The device of claim 1 wherein the at least one micro-lens has a substantially hemispherical and convex outer surface.

5. The device of claim 4 wherein the mating profile is substantially hemispherical and concave.

6. The device of claim 1 wherein at least a portion of the alignment structure is transparent.

7. The device of claim 1 wherein the light source illuminates the at least one micro-lens through the alignment structure.

8. The device of claim 1 wherein the number of micro-lenses is greater than the number of sensors.

9. The device of claim 1 wherein the alignment structure engages fewer than all of the micro-lenses.

10. The device of claim 1 wherein the at least one photo detector is a photo detector array.

11. A sensor alignment system for aligning a sensor array in a biochemical testing device, the sensor array having a plurality of micro-lenses, the sensor alignment system comprising:
    alignment structure positioned in relation to the biochemical testing device and adapted to receive at least two micro-lenses of the micro-lens array in order to align the biochemical testing device with the sensor array, each micro-lens of the micro-lens array has a substantially hemispherical outer surface, the alignment structure having a plurality of substantially hemispherical mating profiles adapted to receive the substantially hemispherical outer surface of at least one micro-lens of the micro-lens array.

12. The sensor alignment system of claim 11 wherein the number of sensors in the sensor array corresponds to the number of micro-lenses in the micro-lens array.

13. The sensor alignment system of claim 11 wherein the alignment structure receives fewer than all the micro-lenses of the micro-lens array.

14. A biochemical testing device for receiving a sensor cartridge, the sensor cartridge having at least one sensor and at least one micro-lens coupled to the sensor such that the micro-lens focuses light into the sensor, the testing device comprising:
    an alignment structure having a mating profile adapted to receive the outer surface of the micro-lens to position the sensor cartridge laterally;
    a light source positioned in relation to the alignment structure for illuminating the at least one micro-lens;
    at least one photo-detector positioned in relation to the alignment structure to detect light emitted from the at least one micro-lens.

15. The biochemical testing device of claim 14 wherein the at least one micro-lens has a convex Outer surface and the mating profile of the alignment structure is substantially concave.

16. The biochemical testing device of claim 14 wherein the alignment structure is transparent.

17. The biochemical testing device of claim 16 wherein the light source illuminates the at least one micro-lens through the alignment structure.

18. The biochemical testing device of claim 14 wherein the alignment structure engages fewer than all of the micro-lenses.

* * * * *